United States Patent [19]

Isaac et al.

[11] Patent Number: 5,907,081
[45] Date of Patent: May 25, 1999

[54] CONTROL OF PLANT ABSCISSION AND POD DEHISCENCE

[75] Inventors: Peter Geoffrey Isaac, Chailly-en-Biére, France; Jeremy Alan Roberts, Longhborough, United Kingdom; Simon Allan Coupe, State College, Pa.

[73] Assignee: Biogemma UK Limited, United Kingdom

[21] Appl. No.: 08/530,165

[22] PCT Filed: Mar. 31, 1994

[86] PCT No.: PCT/GB94/00689

§ 371 Date: Mar. 19, 1996

§ 102(e) Date: Mar. 19, 1996

[87] PCT Pub. No.: WO94/23043

PCT Pub. Date: Oct. 13, 1994

[30] Foreign Application Priority Data

Mar. 31, 1993 [GB] United Kingdom .................. 9306726

[51] Int. Cl.[6] ................ A01H 5/00; C12N 5/14; C12N 15/29; C12N 15/82
[52] U.S. Cl. ............... 800/205; 435/172.3; 435/320.1; 435/419; 536/23.6; 536/24.5
[58] Field of Search .................. 536/23.2, 23.6, 536/24.1, 25.3, 24.5; 435/320.1, 240.1, 240.4, 252.3, 172.3, 419; 800/205; 530/370

[56] References Cited

FOREIGN PATENT DOCUMENTS

| 0 420 819 | 4/1991 | European Pat. Off. . |
|---|---|---|
| WO 91/01375 | 2/1991 | WIPO . |
| WO 91/16426 | 10/1991 | WIPO . |
| WO 92/05261 | 4/1992 | WIPO . |
| 9302197 | 2/1993 | WIPO . |
| WO 93/02197 | 2/1993 | WIPO . |

*Primary Examiner*—David T. Fox
*Assistant Examiner*—Amy J. Nelson
*Attorney, Agent, or Firm*—Sterne Kessler Goldstein & Fox P.L.L.C.

[57] ABSTRACT

Recombinant or isolated nucleic acid sequences which:

(a) encode enzymes or other proteins involved in plant abscission or dehiscence;

(b) contain a promoter or other regulatory sequence which naturally controls expression of a gene involved in plant abscission or dehiscence;

(c) when introduced into a plant, prevent or otherwise interfere with normal plant abscission or dehiscence; or (d) hybridise under stringent conditions to nucleic acid satisfying criterion (a), (b) or (c) or would do so but for the degeneracy of the genetic code are useful in regulating abscission and dehiscence, particularly in reducing pod shatter in *Brassica napus*.

10 Claims, 14 Drawing Sheets

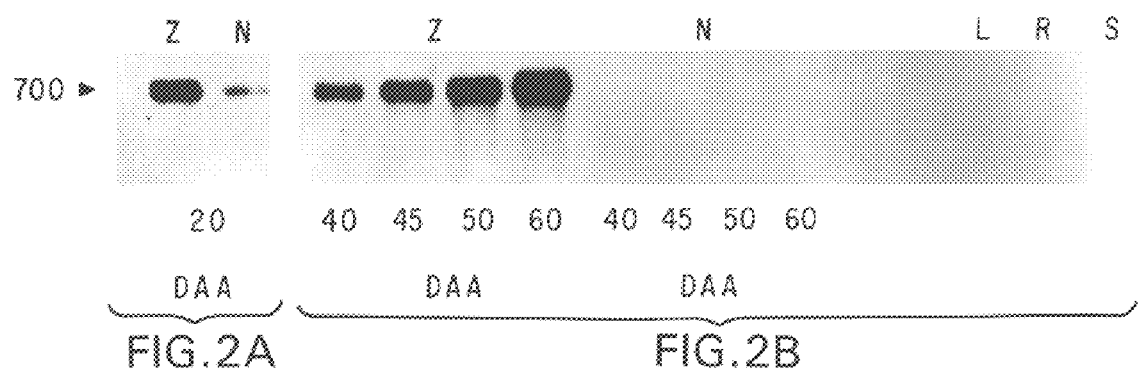

FIG. 3

```
AGAGGAATTAACA                                                              11
              *M  A   S   R   T   K   S   F   L   A   I
              ATG GCT TCA AGA ACG AAA AGC TTT TTA GCC ATT                  47
 F   L   I   N   I   L   F   C   T   T   I   S   A   Y                    26
TTC TTG ATT CTG AAC ATC CTT TTC TGC ACA ACA ATC TCT GCC TAC                92
 G   N   C   G   C   P   S   S   P   K   P   D   P   S                    41
GGT AAC TGC GGT TGC CCT TCT TCT CCC AAG CCA AAA CCT GAC CCC TCC           137
 H   K   P   K   P   N   P   K   P   K   P   T   P   T   P               56
CAT AAG CCA AAA CCT AAC CCT AAA CCT AAA CCC ACC CCA ACT CCA               182
 T   P   S   P   V   T   A   K   C   P   R   D   A   L   K               71
ACC CCT AGC CCT GTC ACA GCC AAA TGC CCT AGA GAC GCT CTT AAA               227
 L   G   C   A   N   V   L   S   G   L   L   N   I   T                   86
CTA GGA TGC GCC AAC GTG CTC AGC GGT CTA CTC AAC ATC ACC                   272
 L   G   K   P   P   V   K   P   C   C   T   C   L   K   G              101
CTT GGG AAG CCA CCT GTG AAG CCA TGT TGT ACC TGC CTC AAA GGA               317
 L   A   D   L   E   A   A   G   I   N   L   T   L   S   K              116
CTT GCT GAT CTT GAA GCC GCG GGG ATC AAC CTG ACC CTC TCA AAG               362
 A   N   I   L   N   V   C   S   K   K   V   P   P   G   F              131
GCT AAC ATC CTT AAC GTT TGT AGC AAA AAG GTT CCC CCT GGT TTC               407
 Q                                                                       146
CAA                                                                      452
 C  *Z                                                                   147
TGC TAA  TCAAGATTATAATTATACAACCACTGGATGTCAACATATATACTTCTT                 509
     *****
GTTTGGATAGACAAGATAATATATGTAATATAGATTCGTAGTATTCTGTGTGTTTAT                 568
GTATGAATTGTATGTGTGTATGTGATTTCTACAACTCTAAACTTCACATTTGTTTTT                 627
ATTTTGTTCTCTTAATTATATACAGTCACAGGGGTGTTGTTGTACTGGTTGTTGTTT                 686
      ******
AAATTAATAATAATATGTTTAATACTGAAAAAAAAAAAAAAAAAAAAAAAAAAAAAAA                745
AAAAAAAAAAA                                                               756
```

```
         1
pSAC51   MASRTKSFLA IFLILNILFC TTISAYGNCG CPSPKPKPDP SHKPKPNPKP
DC2.15   MGSKNSASVA LFFTLNILFF ALVSSTEKC. ......PDP .YKPKPKPTP
pZRP3    MAPK....VA LFLALSLLFA ATAHGCE... ........P NCSGPVVPTP 51                                                100
pSAC51   KPTPTPTPSP VTAKCPRDAL KLGVCANVLS GLLNITLGKP PVKPCCTLIK
DC2.15   KPTPTPYPSA ..GKCPRDAL KLGVCADVLN LVHNVVIGSP PTLPCCSLLE
pZRP3    PVVPTP.SSH SHGRCPIDAL KLKVCAKVLG L....VKVGLP QYEQCCPLLE 101                                               149
pSAC51   GLADLEAAAC LCTALKANIL GINLNIPISL SLLLNVCSKK VPPGFQC..
DC2.15   GLVNLEAAVC LCTAIKANIL GKNLNLPIAL SLVLNNCGKQ VPNGFECT.
pZRP3    GLVDLDAALC LCTAIKANVL GIHLNVPLSL NFILNNCGRI CPEDFTCPN
```

FIG.5

```
                                                            AAATTGAGAGTTTTATCTTCTCTCCTGTACATTATTCTTCTTCACAATCTGC       52
                                                                                                    *M  E   I   Y   G         5
AACATTTTTAATTAGGGTTTCTTAGTTTTGAGAGACATC ATG GTT ACA GGA GCA AAA GGA AAG AGT GGA ATA TAT GGA          106
                                        M   V   T   G   A   K   G   K   S   G   I   Y   G           20
ATG GTT ACA GGA GCA GAT GTC ACT CAC TCC ATT GAT GCC AAA TAC GGA TCA GCA TCA                          151
M   V   T   G   A   D   V   T   H   S   I   D   A   K   Y   G   S   A   S                            35
ACA GCT GAA ATC ACA GGT GGA ACA AGT GGG ATT TTA GAA CAT CTC ACT                                      196
T   A   E   I   T   G   G   T   S   G   I   L   E   H   L   T                                        50
GCC ATC ATC ACA GGT ATG GGA AGT GCT CAT GTC ATT ATC GCG TCA GCA GCA                                  241
A   I   I   T   G   M   G   S   A   H   V   I   I   A   S   R   A                                    65
AGA GTG TTG GGA ATG AGA AGA GGA GCT CAT AAA GAG ATT GAT CTT CAG AGA                                  286
R   V   L   G   M   R   R   G   A   H   K   E   I   D   L   Q   M                                    80
AAC ACA AAA GCA GCA AAC AAC GAT TCT CTT TGT CTT CTC TCT TCT                                          331
N   T   K   A   A   N   D   S   L   C   L   L   S   S                                                95
TAC CCT AAT GCA CGC ATC GAC GAC TTC CAT CAG CAG TTT CTT GCC CTT AAT                                  376
Y   P   N   A   R   I   D   D   F   H   Q   Q   F   L   A   L   N                                   110
ATC AAA TCC GTC AGA TCC ATC ATA AAC AAT AAT GCA GGT GTT ATG TTC TGT                                  421
I   K   S   V   R   S   I   I   N   N   N   A   G   V   M   F   C                                   125
GTC CCT CTC AAC ATA CTC ATA CTC ATA GAT GGG ATT GAA AAT CTT ATG TTC TGT                              466
V   P   L   N   I   L   I   D   G   I   E   N   L   F   A   T                                       140
CCT TTC CAG CTC AGT GAA GAT GGG ATT GAA TCA CAA CTT CTT GCA ACA                                      511
P   F   Q   L   S   E   D   G   I   E   S   Q   L   L   D   K                                       155
AAC CAC ATT GGT CAT TTT CTG TTG ACG AAT CTT CTT CTG GAC AAA                                          556
N   H   I   G   H   F   L   L   T   N   L   L   R   I   V                                           170
ATG AAG AGT AGT GCA CGA GAA AGT GGG ATC GGG GAA AGG ATC GTG                                          601
M   K   S   S   A   R   E   S   G   I   G   E   G   T   E   G   I                                   185
N   L   S   I   A                                           T
```

FIG.8A

```
AAT CTG TCA TCT ATC GCT CAT ACT TAT ACT TAC ACC GAA GGC ATA  646
 M   F   D   Y   I   N   D   T   Y   T   Y   S   E   K   K   200
ATG TTC GAT TAC ATC AAC GAC CCA CGA TAT CGA TAT TCT GAG AAA  691
 A   Y   G   Q   S   K   L   A   N   L   L   Y   S   H   S   215
GCT TAT GGA TCA CAA AAA CTG GCA AAC TTA CAC TTG CAC TCC AAT GCA  736
 L   S   R   K   L   Q   E   E   G   V   N   T   I   T   N   A   230
CTC TCT CGT AAA CTA CAG GAG GAA GGT GTG AAC ATC ACA ATA AAC  781
 S   V   H   P   G   L   I   T   T   N   L   F   R   H   S   245
TCG GTA CAC CCT GGA CTT ATA ACC ACT AAT CTC TTT CGT CAC TCC  826
 G   L   G   M   A   V   L   K   A   S   F   F   V   L   W   260
GGT TTA GGA ATG GCG GTC CTC AAG GCT ATG AGC TTC TTC TTA TGG  871
 K   N   I   P   Q   G   A   D   V   G   G   A   T   C   Y   A   L   275
AAA AAC ATA CCA CAG GGA GCA ACG GGG AAG TAC ACA TGC GTG GCA CTT  916
 H   P   D   L   K   T   A   T   G   K   Y   T   C   V   A   D   C   290
CAT CCT GAT TTA AAA GAC TTA AAA TTC GCC GAC TAC TTC GCG GAC TGT  961
 N   V   T   P   S   N   F   A   T   D   T   L   A   305
AAC GTC ACC ACT CCA AGT AAC TTC GCC GAC ACC CTC GCC TGT  1006
 D   K   L   W   D   F   S   I   K   L   V   E   S   L   P   320
GAT AAA CTT TGG GAT TTC AGT ATA AAA CTC GTC GAG TCT CTT CCC  1051
 *
TAA CTATATATCTAAACGAATTTGTACTCCATAATGTTTTACATTAATTTTATCAGC 1109
ACATATTTGTTTATGGAACTAATATTATAATCAGAAACACCATTGAAAAATAAAAATG 1168
AAATGTAACTAAAAAAAAAAAAAAAAAAAAA 1197
```

FIG.8B

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 756 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 15..458

(xi) SEQUENCE DESCRIPTION: SEQ ID NO: 1:

```
AGAGGAATTT AACA ATG GCT TCA AGA ACG AAA AGC TTT TTA GCC ATT TTC        50
             Met Ala Ser Arg Thr Lys Ser Phe Leu Ala Ile Phe
               1               5                  10

TTG ATT CTG AAC ATC CTT TTC TGC ACA ACA ATC TCT GCC TAC GGT AAC        98
Leu Ile Leu Asn Ile Leu Phe Cys Thr Thr Ile Ser Ala Tyr Gly Asn
         15                  20                  25

TGC GGT TGC CCT TCT CCC AAG CCA AAA CCT GAC CCC TCC CAT AAG CCA       146
Cys Gly Cys Pro Ser Pro Lys Pro Lys Pro Asp Pro Ser His Lys Pro
     30                  35                  40

AAA CCT AAC CCT AAA CCC AAA CCA ACC CCA ACT CCA ACC CCT AGC CCT       194
Lys Pro Asn Pro Lys Pro Lys Pro Thr Pro Thr Pro Thr Pro Ser Pro
 45                  50                  55                  60
```

-continued

```
GTC ACA GCC AAA TGC CCT AGA GAC GCT CTT AAA CTA GGA GTC TGC GCC       242
Val Thr Ala Lys Cys Pro Arg Asp Ala Leu Lys Leu Gly Val Cys Ala
             65                  70                  75

AAC GTG CTC AGC GGT CTA CTC AAC ATC ACC CTT GGG AAG CCA CCT GTG       290
Asn Val Leu Ser Gly Leu Leu Asn Ile Thr Leu Gly Lys Pro Pro Val
                 80                  85                  90

AAG CCA TGT TGC ACC CTC ATC AAA GGA CTT GCT GAT CTT GAA GCC GCG       338
Lys Pro Cys Cys Thr Leu Ile Lys Gly Leu Ala Asp Leu Glu Ala Ala
                     95                 100                 105

GCT TGT CTT TGC ACC GCG CTT AAG GCT AAC ATC CTT GGG ATC AAC CTG       386
Ala Cys Leu Cys Thr Ala Leu Lys Ala Asn Ile Leu Gly Ile Asn Leu
        110                 115                 120

AAC ATC CCT ATC TCA CTC AGT CTG CTT CTC AAT GTT TGT AGC AAA AAG       434
Asn Ile Pro Ile Ser Leu Ser Leu Leu Leu Asn Val Cys Ser Lys Lys
125                 130                 135                 140

GTT CCC CCT GGT TTC CAA TGC TAATCAAGAT TATAATTATA CAACCACCAC          485
Val Pro Pro Gly Phe Gln Cys
                145

TGGATGTCAA CATATATACT TCTTGTTTGG ATAGACAAGA TAATATATGT AATATAGATT     545

CTGTAGTATT TCTGTGTGTT TATGTATGAA TTGTATGTGT GTGTATGTGA TTTCTACAAC     605

TCTAAACTTC ACATTTGTTT TTATTTTGTT CTCTTAATTA TATATACAGT CACAGGGGTG    665

TTGTTGTACT GGTTGTTGTT TAAATTAATA AATAATATGT TTAATACTGA AAAAAAAAA      725

AAAAAAAAAA AAAAAAAAA AAAAAAAAA A                                      756
```

(2) INFORMATION FOR SEQ ID NO: 2:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Ser Arg Thr Lys Ser Phe Leu Ala Ile Phe Leu Ile Leu Asn
  1               5                  10                  15

Ile Leu Phe Cys Thr Thr Ile Ser Ala Tyr Gly Asn Cys Gly Cys Pro
                 20                  25                  30

Ser Pro Lys Pro Lys Pro Asp Pro Ser His Lys Pro Lys Pro Asn Pro
             35                  40                  45

Lys Pro Lys Pro Thr Pro Thr Pro Thr Pro Ser Pro Val Thr Ala Lys
         50                  55                  60

Cys Pro Arg Asp Ala Leu Lys Leu Gly Val Cys Ala Asn Val Leu Ser
 65                  70                  75                  80

Gly Leu Leu Asn Ile Thr Leu Gly Lys Pro Pro Val Lys Pro Cys Cys
                 85                  90                  95

Thr Leu Ile Lys Gly Leu Ala Asp Leu Glu Ala Ala Ala Cys Leu Cys
            100                 105                 110

Thr Ala Leu Lys Ala Asn Ile Leu Gly Ile Asn Leu Asn Ile Pro Ile
        115                 120                 125

Ser Leu Ser Leu Leu Leu Asn Val Cys Ser Lys Lys Val Pro Pro Gly
    130                 135                 140

Phe Gln Cys
145
```

(2) INFORMATION FOR SEQ ID NO: 3:

(i) SEQUENCE CHARACTERISTICS:

(A) LENGTH: 147 amino acids
(B) TYPE: amino acid
(D) TOPOLOGY: linear (ii) MOLECULE TYPE: peptide (xi) SEQUENCE DESCRIPTION: SEQ ID NO: 3:

```
Met Ala Ser Arg Thr Lys Ser Phe Leu Ala Ile Phe Leu Ile Leu Asn
1               5                   10                  15

Ile Leu Phe Cys Thr Thr Ile Ser Ala Tyr Gly Asn Cys Gly Cys Pro
            20                  25                  30

Ser Pro Lys Pro Lys Pro Asp Pro Ser His Lys Pro Lys Pro Asn Pro
        35                  40                  45

Lys Pro Lys Pro Thr Pro Thr Pro Thr Pro Ser Pro Val Thr Ala Lys
    50                  55                  60

Cys Pro Arg Asp Ala Leu Lys Leu Gly Val Cys Ala Asn Val Leu Ser
65                  70                  75                  80

Gly Leu Leu Asn Ile Thr Leu Gly Lys Pro Val Lys Pro Cys Cys
                85                  90                  95

Thr Leu Ile Lys Gly Leu Ala Asp Leu Glu Ala Ala Cys Leu Cys
                100                 105                 110

Thr Ala Leu Lys Ala Asn Ile Leu Gly Ile Asn Leu Asn Ile Pro Ile
            115                 120                 125

Ser Leu Ser Leu Leu Asn Val Cys Ser Lys Lys Val Pro Pro Gly
    130                 135                 140

Phe Gln Cys
145
```

(2) INFORMATION FOR SEQ ID NO: 4:

(i) SEQUENCE CHARACTERISTICS:
(A) LENGTH: 137 amino acids
(B) TYPE: amino acid
(D) TOPOLOGY: linear (ii) MOLECULE TYPE: peptide (xi) SEQUENCE DESCRIPTION: SEQ ID NO: 4:

```
Met Gly Ser Lys Asn Ser Ala Ser Val Ala Leu Phe Phe Thr Leu Asn
1               5                   10                  15

Ile Leu Phe Phe Ala Leu Val Ser Ser Thr Glu Lys Cys Pro Asp Pro
            20                  25                  30

Tyr Lys Pro Lys Pro Lys Pro Thr Pro Lys Pro Thr Pro Thr Pro Tyr
        35                  40                  45

Pro Ser Ala Gly Lys Cys Pro Arg Asp Ala Leu Lys Leu Gly Val Cys
    50                  55                  60

Ala Asp Val Leu Asn Leu Val His Asn Val Val Ile Gly Ser Pro Pro
65                  70                  75                  80

Thr Leu Pro Cys Cys Ser Leu Leu Glu Gly Leu Val Asn Leu Glu Ala
                85                  90                  95

Ala Val Cys Leu Cys Thr Ala Ile Lys Ala Asn Ile Leu Gly Lys Asn
                100                 105                 110

Leu Asn Leu Pro Ile Ala Leu Ser Leu Val Leu Asn Asn Cys Gly Lys
            115                 120                 125

Gln Val Pro Asn Gly Phe Glu Cys Thr
    130                 135
```

(2) INFORMATION FOR SEQ ID NO: 5:

(i) SEQUENCE CHARACTERISTICS:
    (A) LENGTH: 129 amino acids
    (B) TYPE: amino acid
    (D) TOPOLOGY: linear (ii) MOLECULE TYPE: peptide (xi) SEQUENCE DESCRIPTION: SEQ ID NO: 5:

```
Met Ala Pro Lys Val Ala Leu Phe Leu Ala Leu Ser Leu Leu Phe Ala
1               5                   10                  15

Ala Thr Ala His Gly Cys Glu Pro Asn Cys Ser Gly Pro Val Val Pro
            20                  25                  30

Thr Pro Pro Val Val Pro Thr Pro Ser Ser His Ser His Gly Arg Cys
        35                  40                  45

Pro Ile Asp Ala Leu Lys Leu Lys Val Cys Ala Lys Val Leu Gly Leu
    50                  55                  60

Val Lys Val Gly Leu Pro Gln Tyr Glu Gln Cys Cys Pro Leu Leu Glu
65                  70                  75                  80

Gly Leu Val Asp Leu Asp Ala Ala Leu Cys Leu Cys Thr Ala Ile Lys
                85                  90                  95

Ala Asn Val Leu Gly Ile His Leu Asn Val Pro Leu Ser Leu Asn Phe
                100                 105                 110

Ile Leu Asn Asn Cys Gly Arg Ile Cys Pro Glu Asp Phe Thr Cys Pro
            115                 120                 125

Asn
```

(2) INFORMATION FOR SEQ ID NO:6:

(i) SEQUENCE CHARACTERISTICS:
    (A) LENGTH: 1197 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 92..1051

(xi) SEQUENCE DESCRIPTION: SEQ ID NO:6:

```
AAATTGAGAG TTTTATCTTC TCTCCTGTAC ATTATTCTTC TTCACAATCT GCAACATTTT      60

TAATTAGGGT TTCTTAGTTT TGAGAGACAT C ATG GAG ATA TAT GGA ATG GTT        112
                                  Met Glu Ile Tyr Gly Met Val
                                  1               5

ACA GGA AAA GCA GGA AAG AGT GGA TAC GGA TCA GCA TCA ACA GCT GAA       160
Thr Gly Lys Ala Gly Lys Ser Gly Tyr Gly Ser Ala Ser Thr Ala Glu
        10                  15                  20

GAT GTC ACT CAC TCC ATT GAT GCC AAA CAT CTC ACT GCC ATC ATC ACA       208
Asp Val Thr His Ser Ile Asp Ala Lys His Leu Thr Ala Ile Ile Thr
    25                  30                  35

GGT GGA ACA AGT GGG ATT GGA TTA GAA GCA GCA AGA GTG TTG GGA ATG       256
Gly Gly Thr Ser Gly Ile Gly Leu Glu Ala Ala Arg Val Leu Gly Met
40                  45                  50                  55

AGA GGA GCT CAT GTC ATT ATC GCG TCA AGA AAC ACA AAA GCA GCT AAC       304
Arg Gly Ala His Val Ile Ile Ala Ser Arg Asn Thr Lys Ala Ala Asn
                60                  65                  70

GAT TCT AAA GAG ATG ATT CTT CAG ATG TAC CCT AAT GCA CGC ATC GAC       352
Asp Ser Lys Glu Met Ile Leu Gln Met Tyr Pro Asn Ala Arg Ile Asp
            75                  80                  85
```

| | | | | | | | | | | | | | | | |
|---|---|---|---|---|---|---|---|---|---|---|---|---|---|---|---|
| TGT | CTT | CAG | CTT | GAT | CTC | TCT | TCT | ATC | AAA | TCC | GTC | AGA | TCC | TTC | ATC | 400 |
| Cys | Leu | Gln | Leu | Asp | Leu | Ser | Ser | Ile | Lys | Ser | Val | Arg | Ser | Phe | Ile |
|  |  | 90 |  |  |  | 95 |  |  |  | 100 |  |  |  |  |  |

```
TGT CTT CAG CTT GAT CTC TCT TCT ATC AAA TCC GTC AGA TCC TTC ATC         400
Cys Leu Gln Leu Asp Leu Ser Ser Ile Lys Ser Val Arg Ser Phe Ile
         90                  95                 100

CAT CAG TTT CTT GCC CTT AAT GTC CCT CTC AAC ATA CTC ATA AAC AAT         448
His Gln Phe Leu Ala Leu Asn Val Pro Leu Asn Ile Leu Ile Asn Asn
        105                 110                 115

GCA GGT GTT ATG TTC TGT CCT TTC CAG CTC AGT GAA GAT GGG ATT GAA         496
Ala Gly Val Met Phe Cys Pro Phe Gln Leu Ser Glu Asp Gly Ile Glu
120                 125                 130                 135

TCA CAA TTC GCA ACA AAC CAC ATT GGT CAT TTT CTG TTG ACG AAT CTT         544
Ser Gln Phe Ala Thr Asn His Ile Gly His Phe Leu Leu Thr Asn Leu
            140                 145                 150

CTT CTG GAC AAA ATG AAG AGT AGT GCA CGA GAA AGT GGG ATC GAA GGA         592
Leu Leu Asp Lys Met Lys Ser Ser Ala Arg Glu Ser Gly Ile Glu Gly
                155                 160                 165

AGG ATC GTG AAT CTG TCA TCT ATC GCT CAT ACT TAT ACT TAC ACC GAA         640
Arg Ile Val Asn Leu Ser Ser Ile Ala His Thr Tyr Thr Tyr Thr Glu
        170                 175                 180

GGC ATA ATG TTC GAT TAC ATC AAC GAC CCA GAT CGA TAT TCT GAG AAA         688
Gly Ile Met Phe Asp Tyr Ile Asn Asp Pro Asp Arg Tyr Ser Glu Lys
        185                 190                 195

AAA GCT TAT GGA CAG TCA AAA CTG GCA AAC TTA TTG CAC TCC AAT GCA         736
Lys Ala Tyr Gly Gln Ser Lys Leu Ala Asn Leu Leu His Ser Asn Ala
200                 205                 210                 215

CTC TCT CGT AAA CTA CAG GAG GAA GGT GTG AAC ATC ACA ATA AAC TCG         784
Leu Ser Arg Lys Leu Gln Glu Glu Gly Val Asn Ile Thr Ile Asn Ser
                220                 225                 230

GTA CAC CCT GGA CTT ATA ACC ACT AAT CTC TTT CGT CAC TCC GGT TTA         832
Val His Pro Gly Leu Ile Thr Thr Asn Leu Phe Arg His Ser Gly Leu
            235                 240                 245

GGA ATG GCG GTC CTC AAG GCT ATG AGC TTC TTC TTA TGG AAA AAC ATA         880
Gly Met Ala Val Leu Lys Ala Met Ser Phe Phe Leu Trp Lys Asn Ile
                250                 255                 260

CCA CAG GGA GCA GCA ACG ACA TGC TAC GTG GCA CTT CAT CCT GAT TTA         928
Pro Gln Gly Ala Ala Thr Thr Cys Tyr Val Ala Leu His Pro Asp Leu
        265                 270                 275

AAA GAC GTC ACC GGG AAG TAC TTC GCG GAC TGT AAC GTC ACC ACT CCA         976
Lys Asp Val Thr Gly Lys Tyr Phe Ala Asp Cys Asn Val Thr Thr Pro
280                 285                 290                 295

AGT AAC TTC GCC ACC GAC ACT ACC CTC GCC GAT AAA CTT TGG GAT TTC         1024
Ser Asn Phe Ala Thr Asp Thr Thr Leu Ala Asp Lys Leu Trp Asp Phe
                300                 305                 310

AGT ATA AAA CTC GTC GAG TCT CTT CCC TAACTATATA TCTAAACGAA              1071
Ser Ile Lys Leu Val Glu Ser Leu Pro
            315                 320

TTTGTACTCC ATAATGTTTT ACATTAATTT TTATCAGCAC ATATTTGTTT ATGGAACTAA       1131

TATTATAATC AGAAACACCA TTGAAAAAAT AAAAATGAAA TGTAACTAAA AAAAAAAAAA       1191

AAAAAA                                                                 1197
```

(2) INFORMATION FOR SEQ ID NO:7:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:7:

```
Met Glu Ile Tyr Gly Met Val Thr Gly Lys Ala Gly Lys Ser Gly Tyr
 1               5                  10                  15
```

-continued

```
Gly Ser Ala Ser Thr Ala Glu Asp Val Thr His Ser Ile Asp Ala Lys
            20                  25                  30

His Leu Thr Ala Ile Ile Thr Gly Gly Thr Ser Gly Ile Gly Leu Glu
            35                  40                  45

Ala Ala Arg Val Leu Gly Met Arg Gly Ala His Val Ile Ile Ala Ser
            50                  55                  60

Arg Asn Thr Lys Ala Ala Asn Asp Ser Lys Glu Met Ile Leu Gln Met
 65                  70                  75                  80

Tyr Pro Asn Ala Arg Ile Asp Cys Leu Gln Leu Asp Leu Ser Ser Ile
                 85                  90                  95

Lys Ser Val Arg Ser Phe Ile His Gln Phe Leu Ala Leu Asn Val Pro
            100                 105                 110

Leu Asn Ile Leu Ile Asn Asn Ala Gly Val Met Phe Cys Pro Phe Gln
            115                 120                 125

Leu Ser Glu Asp Gly Ile Glu Ser Gln Phe Ala Thr Asn His Ile Gly
    130                 135                 140

His Phe Leu Leu Thr Asn Leu Leu Leu Asp Lys Met Lys Ser Ser Ala
145                 150                 155                 160

Arg Glu Ser Gly Ile Glu Gly Arg Ile Val Asn Leu Ser Ser Ile Ala
                165                 170                 175

His Thr Tyr Thr Tyr Thr Glu Gly Ile Met Phe Asp Tyr Ile Asn Asp
            180                 185                 190

Pro Asp Arg Tyr Ser Glu Lys Lys Ala Tyr Gly Gln Ser Lys Leu Ala
            195                 200                 205

Asn Leu Leu His Ser Asn Ala Leu Ser Arg Lys Leu Gln Glu Glu Gly
    210                 215                 220

Val Asn Ile Thr Ile Asn Ser Val His Pro Gly Leu Ile Thr Thr Asn
225                 230                 235                 240

Leu Phe Arg His Ser Gly Leu Gly Met Ala Val Leu Lys Ala Met Ser
                245                 250                 255

Phe Phe Leu Trp Lys Asn Ile Pro Gln Gly Ala Ala Thr Thr Cys Tyr
            260                 265                 270

Val Ala Leu His Pro Asp Leu Lys Asp Val Thr Gly Lys Tyr Phe Ala
            275                 280                 285

Asp Cys Asn Val Thr Thr Pro Ser Asn Phe Ala Thr Asp Thr Thr Leu
    290                 295                 300

Ala Asp Lys Leu Trp Asp Phe Ser Ile Lys Leu Val Glu Ser Leu Pro
305                 310                 315                 320
```

CONTROL OF PLANT ABSCISSION AND POD DEHISCENCE

This invention relates generally to the control of plant abscission and pod dehiscence or shatter.

BACKGROUND OF THE INVENTION

Abscission is the process that causes the shedding of a range of plant parts, including leaves, flowers and fruit. The process occurs at precise sites and involves coordinated cell wall breakdown. Associated with cell separation is an increase in the activity of several hydrolytic enzymes including, β-1,4-glucanase (cellulase, EC 3.1.2.4) and polygalacturonase (PG EC 3.2.1.15).

The process of pod dehiscence, or shatter as it is commonly termed, in oilseed rape (*Brassica napus*) and other crops shares a number of features with abscission. Degradation and separation of cell walls occurs along a discrete layer of cells, termed the dehiscence zone, and a localised increase in the activity of cellulase has been reported prior to the onset of dehiscence (Meakin and Roberts *J. Exp. Bot.* 41(229) 995–1002 (1990) and *J. Exp. Bot.* 41(229) 1003–1011 (1990)). This process is agronomically important because it may result in the premature shedding of seed before the crop can be harvested. Adverse weather conditions can exacerbate the process resulting in a greater than 50% loss of seed. This loss of seed not only has a dramatic effect on yield but also results in the emergence of the crop as a weed in the subsequent growing season.

Attempts to solve this problem over the last 20 years have focused on the breeding of shatter-resistant varieties. The most commonly used method is by trying to introduce germplasm from related species by interspecific hybridisation. Related species such as *B. nigra, B. juncea* and *B. campestris* have been used for this purpose but resulting plants from these crosses are frequently sterile and lose favourable characteristics which have to be regained by back crossing. This is both time consuming and laborious. The interspecific hybridisation strategy also has to cope with transferring two or more genes which are recessive in action into each of the breeding lines. Indeed, even within *B. campestris*, different genetic backgrounds have revealed different numbers of genes to be important in shatter resistance. This has necessitated breeders performing test crosses at each generation during the attempt to produce elite material. These difficulties have been compounded by the fact that shattering is a difficult and time-consuming trait to assess in the field. All these factors may account for the fact that the conventional breeding approach has made no progress over the last twenty years.

Other methods employed to try and alleviate the problem include chemicals, in the form of desiccants and pod sealants. The most widely used method to try and prevent seed loss is the mechanical technique of swathing in order to get uniform desiccation of the crop and reduce shattering by wind which occurs in the upright crop.

SUMMARY OF THE INVENTION

This invention takes a completely different approach to solve the problem of dehiscence and the related problem of adequately controlling plant abscission: it involves the use of recombinant DNA technology. In 1988, when plant biotechnology had reached an age of some considerable sophistication, Roberts and Taylor speculated:

By regulating cell separation at abscission sites, it may be possible . . . to also influence related processes such as pod dehiscence. (*Proceedings of the Symposium on the Physiology of Fruit Drop, Ripening, Storage and Post-Harvest Processing of Fruits*, Turin, Oct. 3–4, 1988, pp 24–33).

However, without any indication of which genes may be involved in such processes, this exhortation did little to enable the art to address the problem at the cell or genetic level.

It has now been discovered that there are genes whose expression is, spatially and/or temporally, specific or at least preferential for tissue involved in abscission or dehiscence. The invention relates to the exploitation of such genes and related DNA sequences (including regulatory sequences) in the manipulation of plant abscission in general and the reduction or prevention of pod dehiscence in particular.

According to a first aspect of the present invention, there is provided a recombinant or isolated nucleic acid sequence which:

(a) encodes an enzyme or other protein involved in plant abscission or dehiscence;

(b) contains a promoter or other regulatory sequence which naturally controls expression of a gene involved in plant abscission or dehiscence;

(c) when introduced into a plant, prevents or otherwise interferes with normal plant abscission or dehiscence; or (d) hybridises under stringent conditions to nucleic acid satisfying criterion (a), (b) or (c) or would do so but for the degeneracy of the genetic code.

The recombinant or isolated nucleic acid will generally be DNA, but RNA is not excluded from the scope of the invention.

At its broadest, the invention is applicable generally to plant abscission or dehiscence, that is to say to the organised shedding of a part of a plant by means of an absciss layer or dehiscence zone. Parts of plants that may from time to time be involved in abscission include leaves, petals, pods, seeds and fruit. The invention may also have application in regulating the abscission of pollen from anthers, which may be useful in generating artificially male sterile plants, which are useful for hybrid seed production (as, for example, discussed in WO-A-9211379).

In the embodiments of the invention relating to dehiscence, the invention has application to all crops that lose seed pre-harvest because of cell separation events. An economically important crop to which the invention applies is Brassica napus.

Recombinant or isolated nucleic acid sequences which satisfy criterion (a) given above are illustrated by the nucleic acid sequence of FIGS. 3 (SEQ ID NO:1), 8A and 8B (SEQ ID NO:6), which encode the amino acid sequences shown in those figures. All other nucleic acid sequences which, by virtue of the degeneracy of the genetic code, also code for the given amino acid sequences are also preferred embodiments of the invention. Nucleic acid sequences which are substantially homologous to nucleic acid sequences encoding the amino acid sequences shown in FIGS. 3 (SEQ ID NOS:1,2), 8A and 8B (SEQ ID NOS:6,7) also constitute preferred embodiments of the invention. "Substantial homology" may be assessed either at the nucleic acid level or at the amino acid level. At the nucleic acid level, sequences having substantial homology may be regarded as those which hybridise to the nucleic acid sequences shown in FIGS. 3, 8A and 8B under stringent conditions (for example at 35 to 65° C. in a salt solution of about 0.9M). At the amino acid level, a protein sequence may be regarded as substantially homologous to another protein sequence if a significant number of the constituent amino acids exhibit homology. At least 40%, 50%, 60%, 70%, 80%, 90%, 95% or even 99%, in increasing order of preference, of the amino acids may be homologous. Specifically excluded from nucleic acids satisfying the criterion of (a) are nucleic acids encoding the DC2.15 (SEQ ID NO:4) and pZRP3 (SEQ ID NO:5) sequences shown in FIG. 5. Nucleic acids encoding plant abscission or dehiscence proteins having one or more amino acids of pSAC51 (SEQ ID NO: 3) not shared with at least one of DC2.15 and pZRP3 are, however, within the scope of the invention.

The most preferred embodiments of the invention satisfying criterion (a) are nucleic acids encoding proteins specifically or at least preferentially expressed in the dehiscence zone of pericarp tissue, particularly in *Brassica napus*.

Nucleic acid satisfying criterion (b) given above constitutes a powerful and flexible means of achieving the benefits of the invention. Such nucleic acid contains a promoter or other regulatory sequence which naturally controls expression of a gene involved in plant abscission or dehiscence. The promoter is that region of a gene which regulates its expression, for example by specifying the time or location of expression. Promoters can be separated from the coding region of a gene and used to drive a different coding region, thus allowing the expression of a different product.

In one implementation of the invention under this general heading, the promoter may drive a gene which disrupts cellular development. For example, the promoter may drive DNA coding a lytic enzyme. The lytic enzyme may cause lysis of one or more biologically important molecules, such as macromolecules including nucleic acid, protein (or glycoprotein), carbohydrate and in some circumstances lipid.

Ribonuclease (such as RNase T1) and barnase are examples of enzymes which cause lysis of RNA. Examples of enzymes which lyse DNA include exonucleases and endonucleases, whether site specific (such as EcoRI) or non-site-specific. Glucanase is an example of an enzyme which causes lysis of a carbohydrate. Lipases whose corresponding nucleic acids may be useful in the invention include phospholipase $A_2$. Actinidin is an example of a protease, DNA coding for which may be useful in the invention; other examples include papain zymogen and papain active protein. Such "killer" enzymes as these do not have to be lytic enzymes. Other examples of enzymes DNA coding for which may be useful in the invention catalyse the synthesis of phytohormones, such as isopentyl transferase, which is involved in cytokinin synthesis, and one or more of the enzymes involved in the synthesis of auxin.

While promoters useful in feature (b) of the invention may drive DNA encoding an enzyme, they may alternatively drive DNA whose transcription product is itself deleterious. Examples of such transcription products include antisense RNA and ribozymes.

As far as antisense nucleic acid is concerned, introducing the coding region of a gene in the reverse orientation to that found in nature can result in the down-regulation of the gene and hence the production of less or none of the gene product. The RNA transcribed from antisense DNA is capable of binding to, and destroying the function of, a sense RNA of the sequence normally found in the cell, thereby disrupting function. Examples of such antisense DNAs are the antisense DNAs of the sequences shown in FIGS. 3 (SEQ ID NO:1), 8A and 8B (SEQ ID NO:6). Since these genes are normally expressed in the dehiscence zone, antisense to them may be expected to disrupt normal dehiscence.

Ribozymes are RNA "enzymes" C.apable of highly specific cleavage against a given target sequence (Haseloff and Gerlach, *Nature* 334 585–591 (1988)).

Promoters useful in feature (b) of the invention may be located in cDNA or genomic libraries using, for example, probe sequences taken from the nucleic acid sequences of FIGS. 3 (SEQ ID NO:1), 8A and 8B (SEQ ID NO:6).

A third category of nucleic acid useful in the invention is identified under (c) above, as that which, when introduced into a plant, prevents or otherwise interferes with normal plant abscission of dehiscence. Generally this would be achieved by interfering with the proper expression of one or more genes involved in abscission or dehiscence. Of course, dehiscence- or abscission-specific promoters, as discussed under (b) above, may be useful in this feature of the invention. However, there is a broader dimension which must be considered: antisense DNA or ribozyme-encoding DNA specific for abscission- or dehiscence-specific genes need not be driven by abscission- or dehiscence-specific promoters. Instead, they could be driven by constitutive or other promoters (such as for example the CaMV 35S, rubisco or plastocyanin promoter). As the sense gene is only expressed in the pod, there will with an antisense approach be no pleiotropic effects on plant development, and only the development of the dehiscence zone will be disruptive. A ribozyme gene expressed throughout the plant will not result in a translated protein product, and so may require less metabolic energy than the synthesis of a gene product throughout most of the plant.

Antisense technology and ribozyme technologies have already found application in other areas of plant molecular biology. For example, antisense technology has been used to control tomato fruit ripening. Ribozyme technology has been used to control viral infection of melons.

While DNA or RNA in accordance with this feature of the invention generally interferes with the proper expression of a gene or genes, in preferred embodiments expression is substantially prevented.

Another important group of nucleic acids useful in the invention is specified under feature (d); this includes nucleic acids which hybridise under stringent conditions to nucleic acids satisfying the criterion of one or more of features (a), (b) or (c). For example, nucleic acid fragments are useful for probing for similar genes involved in abscission or dehiscence. For example, an Arabidopsis or other gene library may be probed. Fragments of at least 10, 20, 30, 40 or 50 more nucleotides may be used. Many useful probes are from 15 to 20 nucleotides in length.

In preferred embodiments of DNA sequences of this invention, 3'-transcription regulation signals, including a polyadenylation signal, may be provided. Preferred 3'-transcription regulation signals may be derived from the cauliflower mosaic virus 35S gene. It should be recognised that other 3'-transcription regulation signals could also be used.

Recombinant DNA in accordance with the invention may be in the form of a vector. The vector may for example be a plasmid, cosmid or phage. Vectors will frequently include one or more selectable markers to enable selection of cells transfected (or transformed: the terms are used interchangeably in this specification) with them and, preferably, to enable selection of cells harbouring vectors incorporating heterologous DNA. Appropriate start and stop signals will generally be present. Additionally, if the vector is intended for expression, sufficient regulatory sequences to drive expression will be present; however, DNA in accordance with the invention will generally be expressed in plant cells, and so microbial host expression would not be among the primary objectives of the invention, although it is not ruled out. Vectors not including regulatory sequences are useful as cloning vectors.

Cloning vectors can be introduced into *E. coli* or another suitable host which facilitate their manipulation. According to another aspect of the invention, there is therefore provided a host cell transfected or transformed with DNA as described above.

DNA in accordance with the invention can be prepared by any convenient method involving coupling together successive nucleotides, and/or ligating oligo- and/or polynucleotides, including in vitro processes, but recombinant DNA technology forms the method of choice.

Ultimately, DNA in accordance with the invention will where appropriate be introduced into plant cells, by any suitable means. According to a further aspect of the invention, there is provided a plant cell including DNA in accordance with the invention as described above.

Preferably, DNA is transformed into plant cells using a disarmed Ti-plasmid vector and carried by Agrobacterium by procedures known in the art, for example as described in EP-A-0116718 and EP-A-0270822. Alternatively, the foreign DNA could be introduced directly into plant cells using an electrical discharge apparatus. This method is preferred where Agrobacterium is ineffective, for example where the recipient plant is monocotyledonous. Any other method that provides for the stable incorporation of the DNA within the nuclear DNA of any plant cell of any species would also be suitable. This includes species of plant which are not currently capable of genetic transformation.

Preferably DNA in accordance with the invention also contains a second chimeric gene (a "marker" gene) that enables a transformed plant containing the foreign DNA to be easily distinguished from other plants that do not contain the foreign DNA. Examples of such a marker gene include antibiotic resistance (Herrera-Estrella et al., *EMBO J.* 2(6) 987–95 (1983) and Herrera-Estrella et al., *Nature* 303 209–13 (1983)), herbicide resistance (EP-A-0242246) and glucuronidase (GUS) expression (EP-A-0344029). Expression of the marker gene is preferably controlled by a second promoter which allows expression in cells other than the tapetum, thus allowing selection of cells or tissue containing the marker at any stage of regeneration of the plant. The preferred second promoter is derived from the gene which encodes the 35S subunit of Cauliflower Mosaic Virus (CaMV) coat protein. However any other suitable second promoter could be used.

A whole plant can be regenerated from a single transformed plant cell, and the invention therefore provides transgenic plants (or parts of them, such as propagating material) including DNA in accordance with the invention as described above. The regeneration can proceed by known methods.

A further aspect of the invention is constituted by novel proteins which are preferentially or exclusively expressed in dehiscence zones or abscission layers. Examples of such proteins are those whose amino acid sequences are given in FIGS. 3 (SEQ ID NO:1,2), 8A and 8B (SEQ ID NO:6,7).

Preferred features of each aspect of the invention are as for each other aspect *mutatis mutandis*.

BRIEF DESCRIPTION OF THE FIGURES

The invention will now be illustrated by the following Examples. The Examples refer to the accompanying drawings, in which:

FIGS. 2A and 2B also relate to Example 1 and are Northern blot analysis of total RNA (10 µg). The RNA was hybridised to radiolabelled pSAC51 cDNA insert.

FIG. 2A 20 DAA pod samples given a 48 hour exposure time to illustrate signal in the non-zone sample.

FIG. 2B Later stages of pod development given 15 hour exposure.

Z=Zone, N=Non-Zone, DAA=days after anthesis, L=Leaf, R=Root, S=Seed.

FIG. 3 also relates to Example 1 and shows the nucleotide (SEQ ID NO:1) and deduced amino acid (SEQ ID NO:1,2) sequence of pSAC51 cDNA. The initiation and termination codons are indicated by a single asterisk. Amino acid domains of interest are double underlined and a possible glycosylation site is underlined. A putative polyadenylation signal has asterisks above it.

Figure 4:
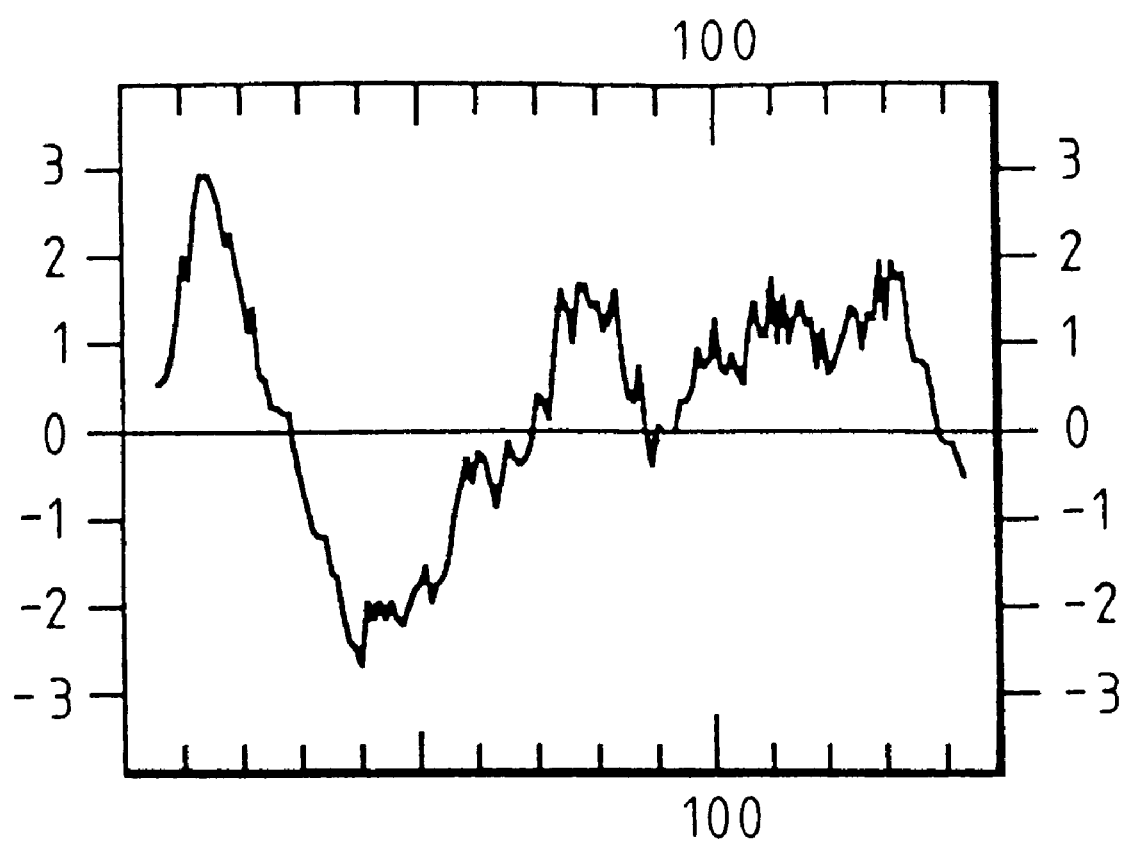

FIG. 4 also relates to Example 1 and shows the hydropathy profile of the cDNA clone pSAC51 deduced amino acid sequence. The profile was computer generated according to Kyte and Doolittle *J. Mol. Biol.* 157 105–132 (1982).

FIG. 5 also relates to Example 1 and shows the sequence alignment of amino acids deduced from nucleotide sequences of the following cDNAs:

pSAC51 (SEQ ID NO:3)—Oilseed rape pods

DC2.15 (SEQ ID NO:4)—Carrot embryos, Aleith and Richter Planta 183, 17–24 (1990)

pZRP3 (SEQ ID NO:5)—Maize roots, John et al, *Plant Mol. Biol.* 20 821–831 (1992)

Common amino acids are in bold.

Figure 6:
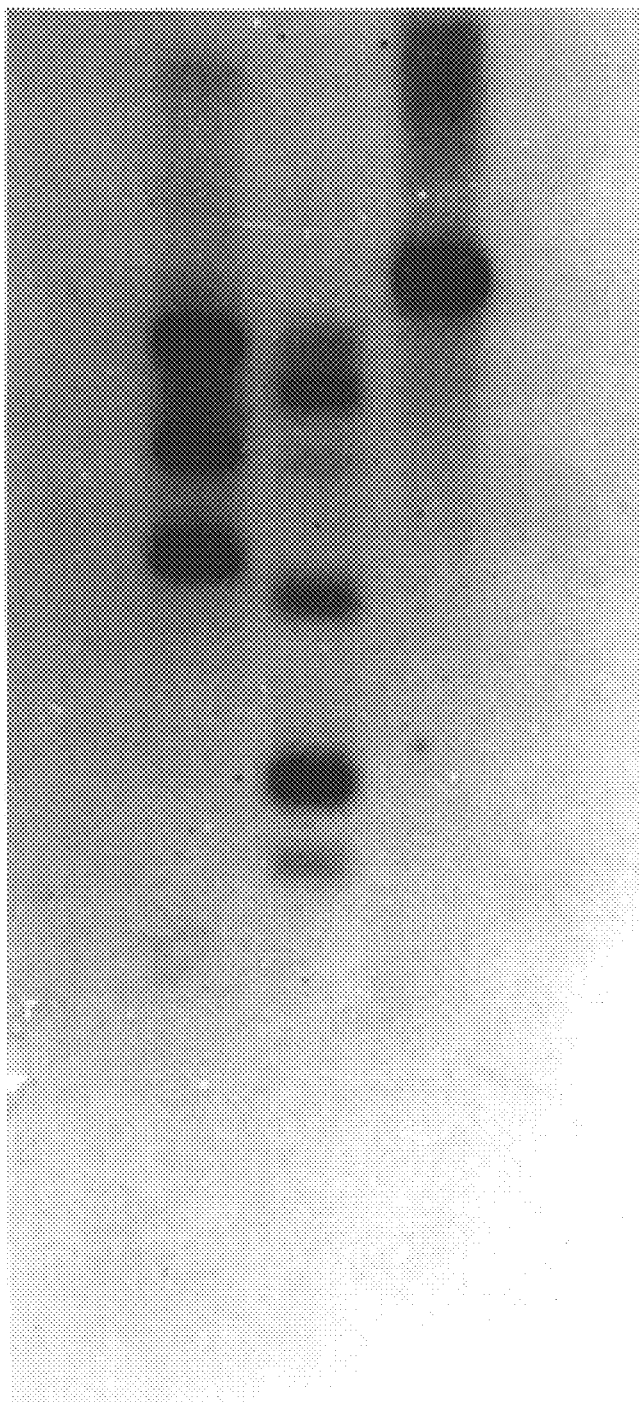

FIG. 6 also relates to Example 1 and shows a genomic Southern blot analysis of *B. napus* DNA probed with the pSAC51 cDNA. 10 µg DNA was digested using the following restriction enzymes: E=EcoRI, H=HindIII, B=BamHI. the positions of HindIII-digested λ DNA markers are also indicated.

Figure 7A:
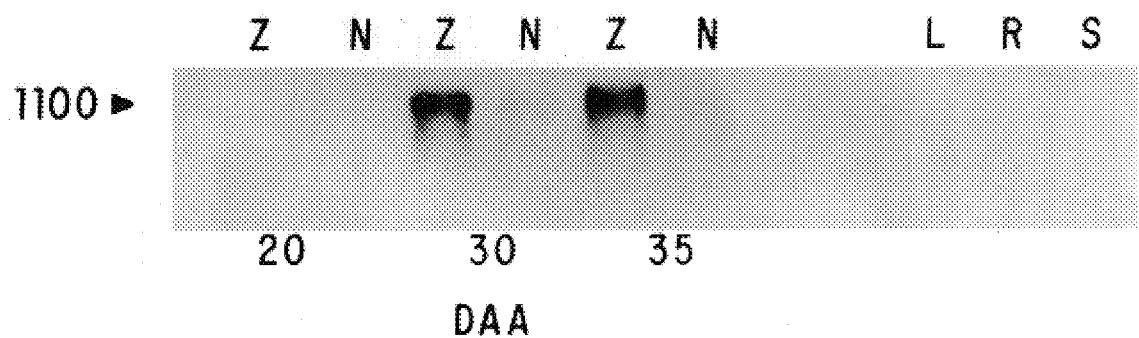
Figure 7B:
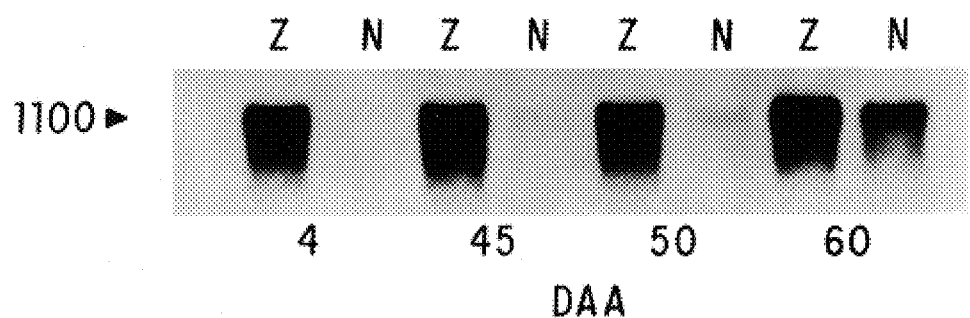

FIGS. 7A and 7B refer to Example 2 and show a Northern blot analysis of total RNA (10 µg). The RNA was hybridised to radiolabelled pSAC25 cDNA insert. Z=Zone, N=Non-Zone, DAA=days after anthesis, L=Leaf, R=Root, S=Seed.

FIGS. 8A and 8B also refer to Example 2 and shows the pSAC40 nucleotide (SEQ ID NO:6) and deduced amino acid (SEQ ID NO:6,7) sequences.

Figure 9:
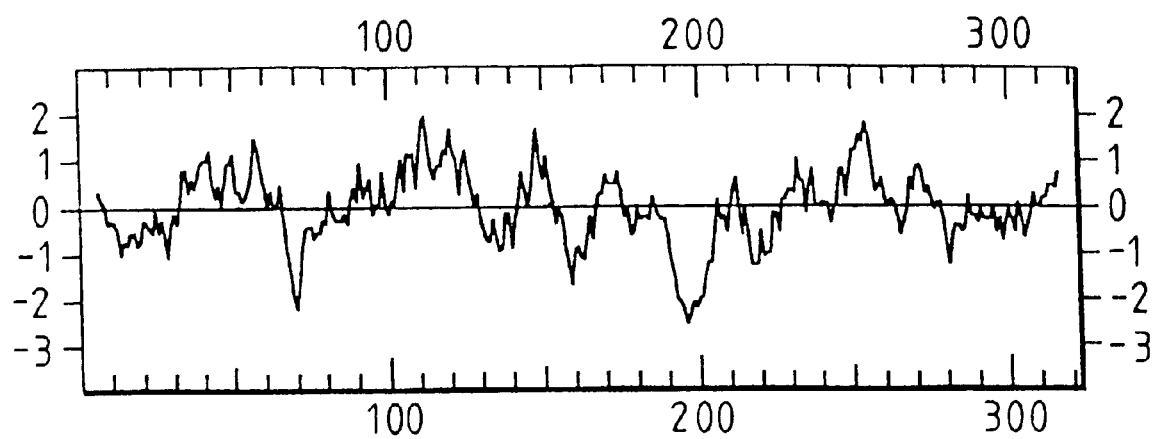

FIG. 9 also refers to Example 2 and shows a hydropathy profile of the cDNA clone pSAC25 deduced amino acid sequence. The profile was computer generated according to Kyte and Doolittle, *J. Mol. Biol.* 157 105–132 (1982).

Figure 10:
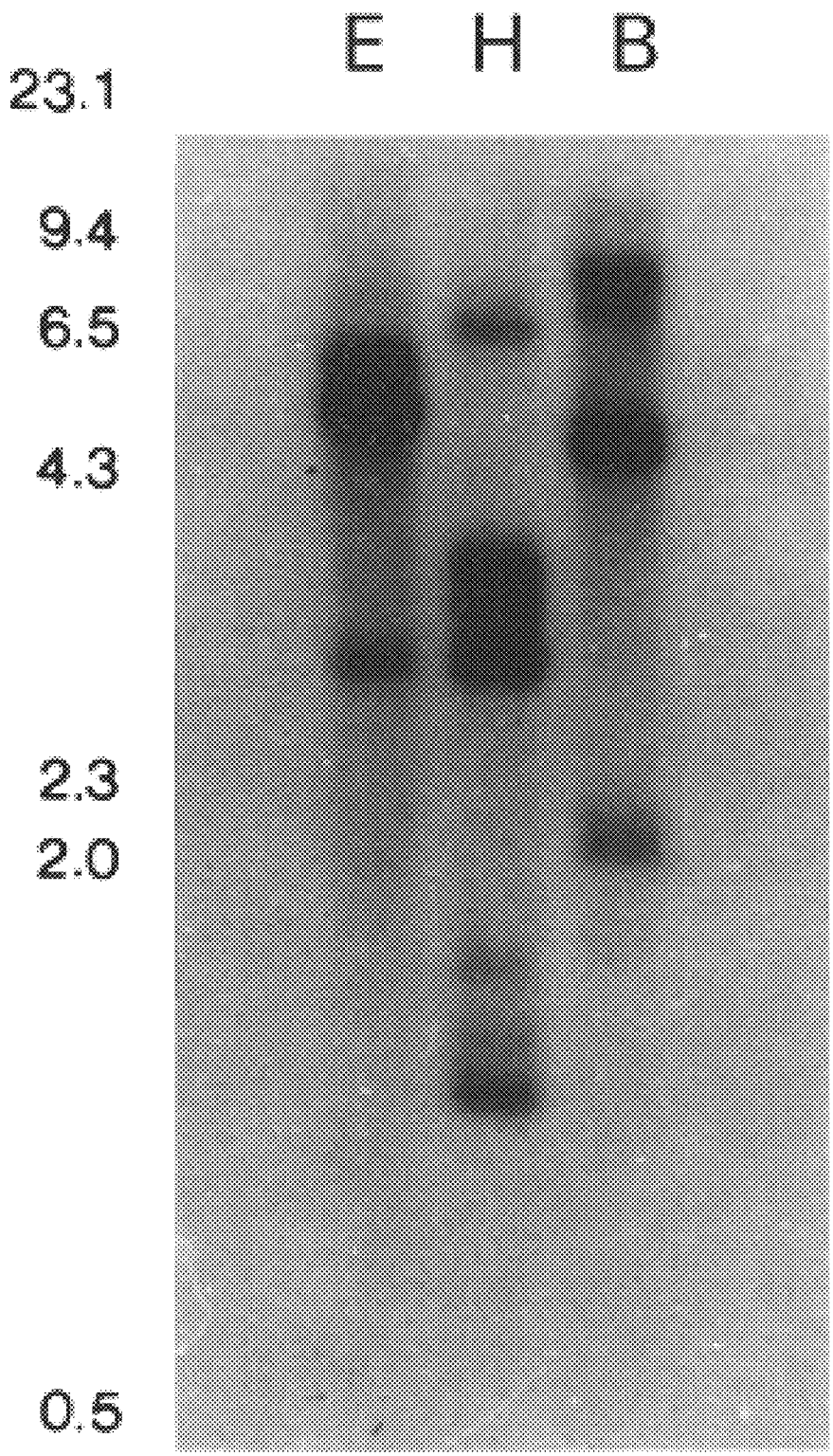

FIG. 10 also refers to Example 2 and shows a genomic Southern blot analysis of *B. napus* DNA probed with the pSAC25 cDNA. 10 µg DNA was digested using the following restriction enzymes: E=EcoRI, H=HindIII, B=BamHI. the position of HindIII digested λ DNA markers are also indicated.

Figure 11A:
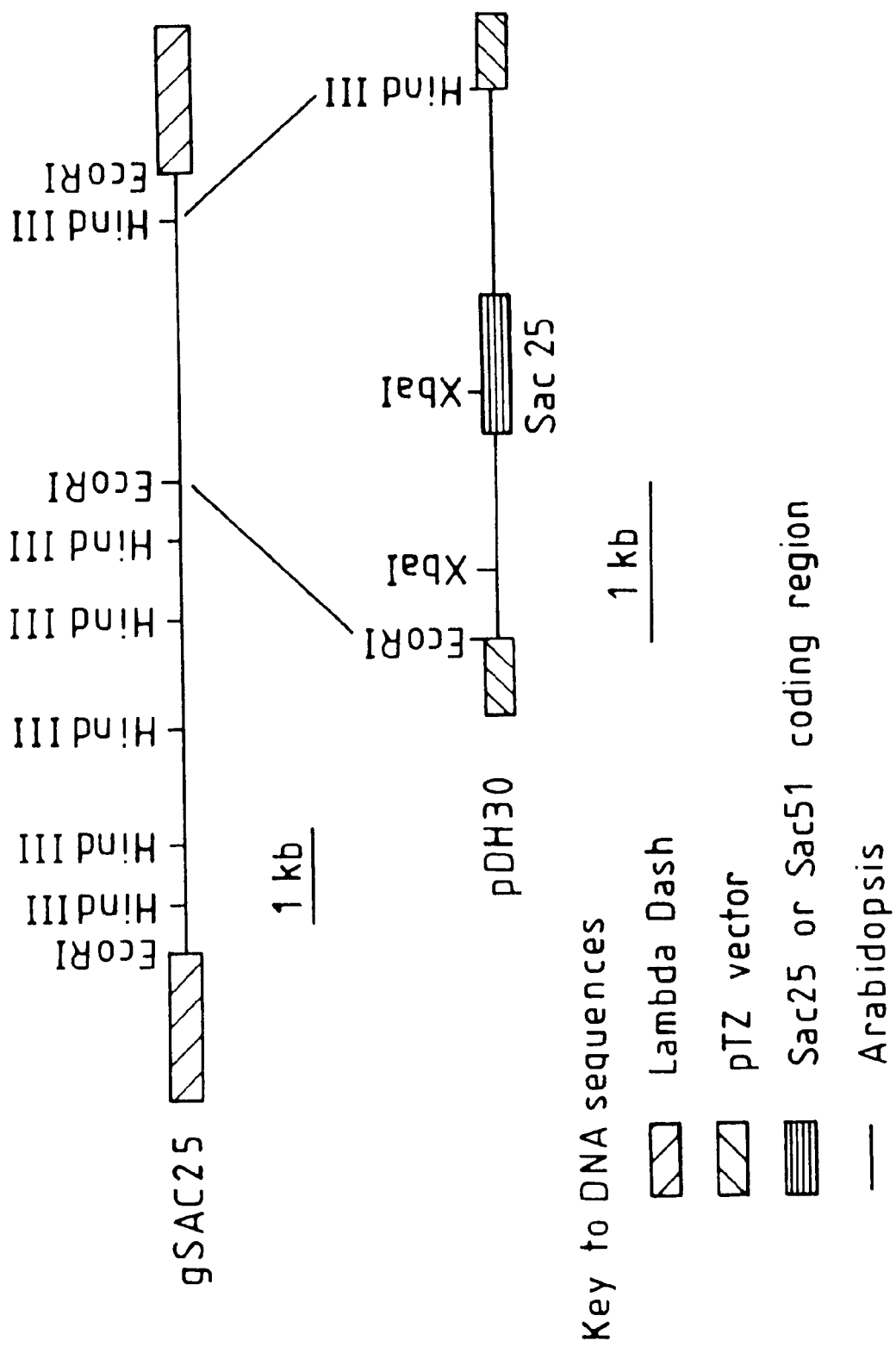
Figure 11B:
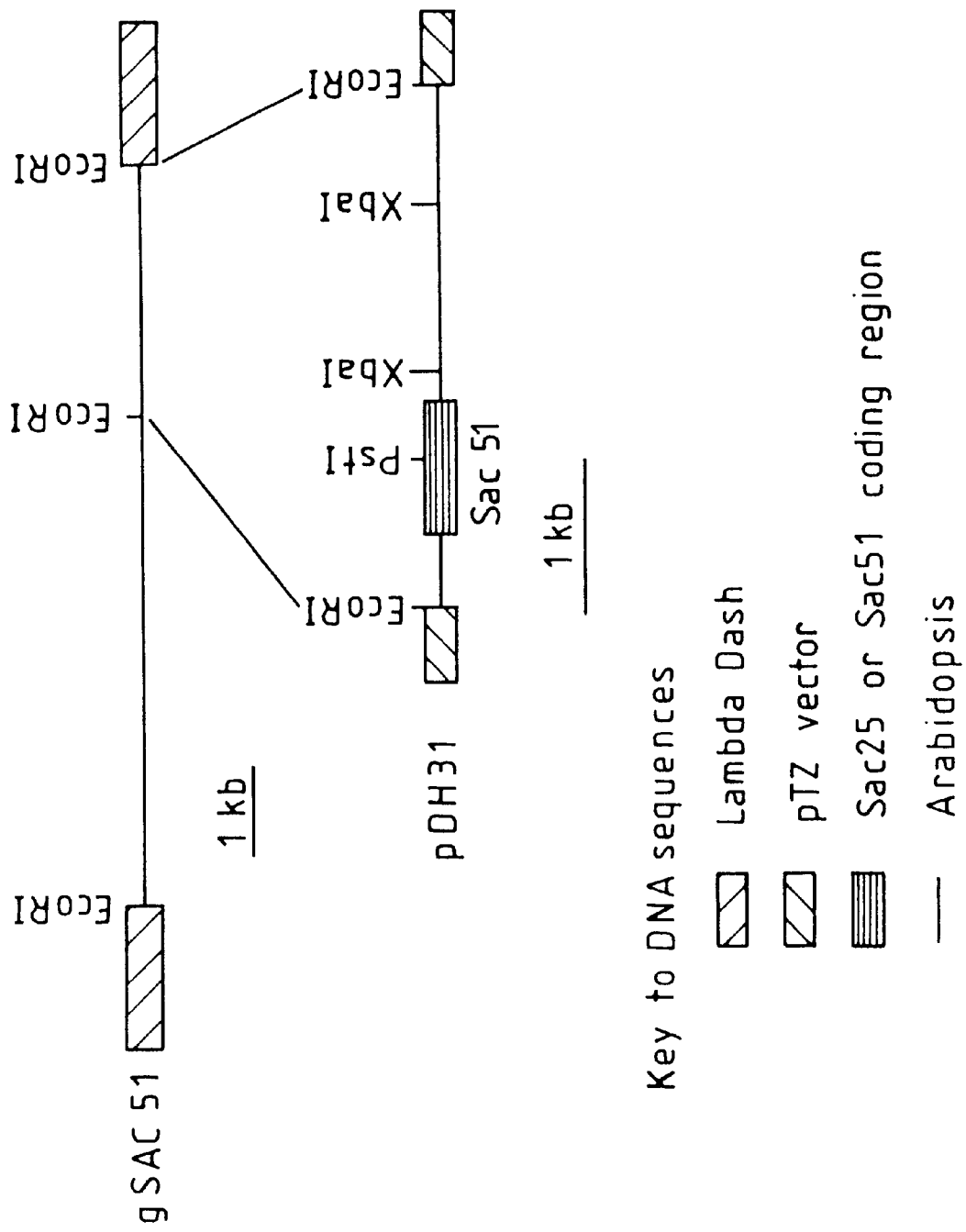

FIG. 11 A shows a restriction map of the *A. thaliana* genomic clone gSAC25. The position of the SAC25 coding region is shown as a filled box and the extent of the insert in pDH30 is indicated.

FIG. 11 B shows a restriction map of the *A. thaliana* genomic clone gSAC51. The position of the SAC51 coding region is shown as a filled box and the extent of the insert in pDH31 is indicated.

Figure 12:
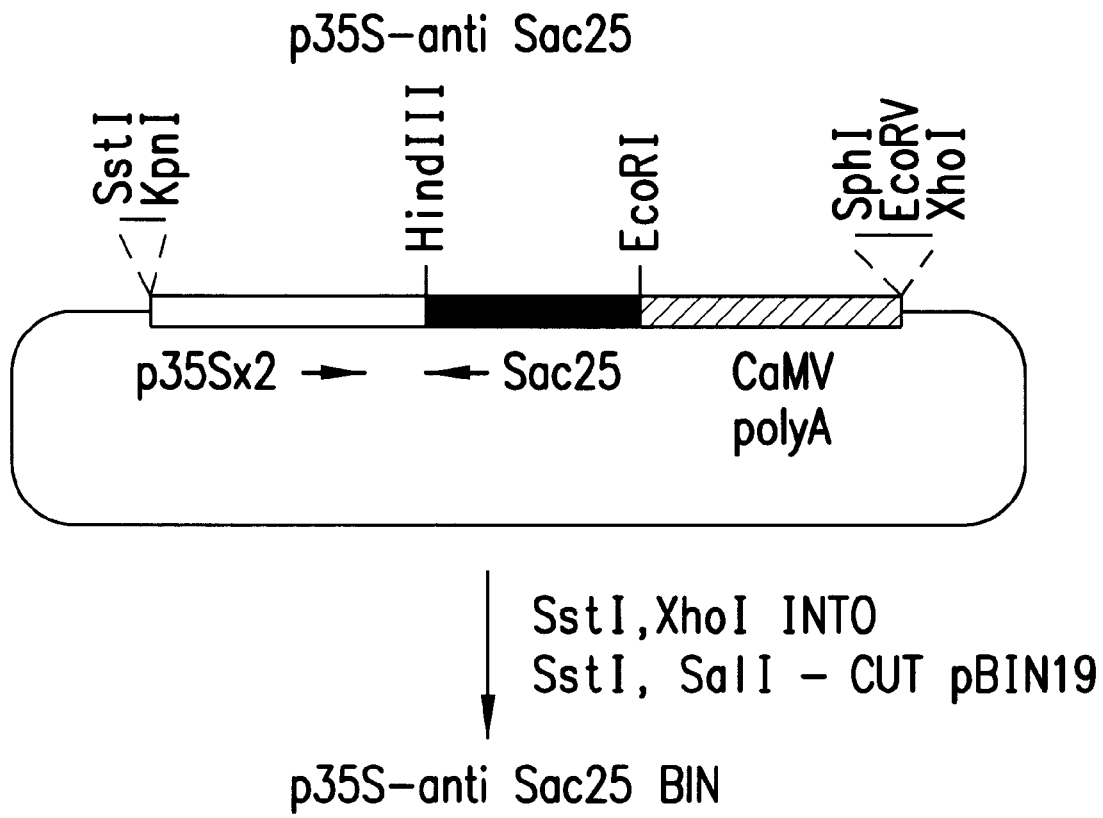

FIG. 12 shows the construction of a chimeric gene that expresses SAC25 anti-sense RNA from the CaMV double 35S promoter in transgenic plants.

DETAILED DESCRIPTION OF THE INVENTION

EXAMPLE 1

Cloning of pSAC51

Plant Material

Seeds of *B. napus* cv *Rafal* were grown as described by Meakin and Roberts, (*J. Exp. Bot.* 41(229) 995–1002

(1990)) with the following modifications. Single seedlings were potted into 10 cm pots, and after vernalization, were re-potted into 21 cm pots. At anthesis tags were applied daily to record flower opening. This procedure facilitated accurate age determination of each pod. Pods were harvested at various days after anthesis (DAA). The dehiscence zone (see FIG. 1) was excised from the non-zone material and seed using a scalpel blade (Meakin and Roberts, *J. Exp. Bot.* 41(229) 1003–1011 (1990)) and immediately frozen in liquid $N_2$ and stored at −70° C.

RNA Isolation

All chemicals were molecular biology grade and bought from either Sigma Chemical Ltd (Dorset, UK), or Fisons (Loughborough, UK). Total RNA was extracted using the polysomal extraction method of Christoffersen and Laties, *Proc. Natl. Acad. Sci.* 79 4060–4063 (1982), with the following alterations. The plant material was ground to a powder in liquid $N_2$ and then in 10 volumes of extraction buffer (200 mM Tris-acetate [pH 8.2], 200 mM magnesium acetate, 20 mM potassium acetate, 20 mM EDTA, 5% w/v sucrose, after sterilisation 2-mercaptoethanol was added to 15 mM and cycloheximide added to a final concentration of 0.1 mg ml$^{-1}$). The supernatant was then layered over 8 ml 1 M sucrose made with extraction buffer and centrifuged in a KONTRON™ (Switzerland) TFT 70.38 rotor at 45,000 rpm (150,000 g) for 2 hr at 2° C. in a Kontron CENTRIKON™ T-1065 ultra-centrifuge. Pellets were then resuspended in 500 µl 0.1M sodium acetate, 0.1% SDS, pH 6.0 and phenol/chloroform (1:1 v/v) extracted and the total RNA precipitated. Poly(A)$^+$ RNA was isolated from total RNA extracted, from both the zone and non-zone tissue of 40, 45 and 50 DAA pods, using a Poly(A) QUIK™ mRNA purification kit (Stratagene, Cambridge, UK) following the manufacturers instructions, and then bulked together. Total RNA was also extracted from leaves, seeds and pods using a method described by Dean et al, *EMBO J.* 4 3055–3061 (1985) for use in Northern analyses.

cDNA Library Construction and Screening

A cDNA library was constructed using 5 µg poly(A)$^+$ RNA extracted from the dehiscence zone of pods prior to and during dehiscence. The library was constructed using the λZAP-cDNA synthesis kit according to the manufacturers' instructions (Stratagene). This resulted in the production of a library containing 1.2×10$^6$ recombinants. Several plaques were picked at random and in vivo excised (Short et al, *Nucl. Acids Res.* 16 7583–7600 (1988)). The average insert size was 1 Kb. Differential screening was performed using single-stranded cDNA probes synthesised from poly (A)$^+$ RNA isolated from dehiscence zone or non-zone pod material. The probes were synthesised using the method of Picton et al, *Plant Mol. Biol* in press (1993) and used to screen 40,000 recombinant plaques by in situ plaque hybridisation. Duplicate plaque lifts were obtained using HYBOND™ N$^+$ membranes (Amersham, Aylesbury, UK) and were then treated and hybridised according to manufacturers instructions but were washed at 65° C. in 0.1× sodium chloride, sodium phosphate, EDTA (SSPE), 0.1% SDS. Any plaques hybridising preferentially to zone probes were re-screened at densities of 50–100 plaques/plate. Chosen plaques were cored out of the plate and plasmids isolated using the in vivo excision procedure (Short et al, *Nucl. Acids Res.* 16 7583–7600 (1988)). Inserts were amplified by polymerase chain reaction (PCR) using the T3, T7 bacteriophage promoters and subsequently used for probes. Isolated plasmid was also used as a template for sequencing.

Northern Blot Analysis of RNA

10 µg total RNA isolated from various parts of the oilseed rape plant were separated on a 1×TBE, 1% agarose/6% formaldehyde denaturing gel. The RNA was transferred onto a nylon membrane (GeneScreen, NEN-Du Pont, UK) using capillary transfer. The gel, RNA samples, blot and hybridisation were performed in accordance with the membrane manufacturers instructions. A radio-labelled probe was generated using 100 ng of insert from the plasmid pSAC51, using [$^{32}$P] dCTP (110 TBq nmole$^{-1}$, Amersham) and a nick translation kit (Boehringer Mannheim, Lewes, UK). Unincorporated label was removed from the probe by passing it through a SEPHADEX™ G-50 column and eluting the probe with TE (pH 8). The blot was washed at 65° C. in 0.1×SSPE, 0.1% SDS and exposed to KODAK™ X-AR5 film with intensifying screens at −70° C.

Genomic DNA Isoation and Characterisation

DNA was isolated, using a miniprep procedure using a modified form of the extraction buffer described by Clarke et al, *Genome* 32 334–339 (1989). Young expanding oilseed rape seedlings were homogenised in a 3.8:0.6:0.6 mixture of the following; TNE buffer (0.05M Tris.HCl pH 7.5, 0.2M EDTA: 0.1M NaCl): 5% SDS: 1 mg ml$^{-1}$ proteinase K; to this solution was added sodium diethyidithiocarbamate and sodium bisulphite to 0.4% (w/v) just before use. The samples were then incubated for 1 hr at 37° C. and debris removed by centrifugation in a microfuge at 11,600 g for 5 min. The eluate was then extracted with equal volumes of phenol/chloroform (1:1 v/v) and then chloroform alone. Nucleic acids were then precipitated by the addition of 2.5 vols 95% ethanol containing 5% (v/v) 2M Na acetate, pH 5.5. The sample was then mixed and immediately centrifuged at 11,600 g for 5 min. The resulting pellet was resuspended in 300 µl TE, 10 µl RNaseA (10 mg ml$^{-1}$) added, and then incubated at 37° C. for 15 mins before 300 µl CTAB buffer (0.2M Tris.HCl pH 7.5, 0.05M EDTA, 2M NaCl and 2% w/v CTAB) was added before a further incubation at 60° C. for 15 mins. Following re-extraction with an equal volume of chloroform the DNA was precipitated with an equal volume of isopropanol at −20° C. Subsequent digestions by restriction endonucleases were carried out as detailed in Stacey and Isaac, Restriction enzyme digestion, gel electrophoresis and vacuum blotting of DNA to nylon membranes (1993). The DNA was then separated in 1×TBE, 0.8% agarose and transferred to GENESCREEN+™ (NEN) nylon membrane. The probes were made as described for Northern analysis and hybridisation was carried out according to manufacturers recommendations. The final wash of the membrane was at 65° C. in 0.1×sodium chloride, sodium citrate (SSC) 0.1% SDS.

DNA Sequencing

Plasmid DNA was isolated by the alkaline-lysis method (Sambrook et al, *Molecular Cloning: A Laboratory Manual* New York, Cold Spring Harbour Laboratory Press (1989)). Supercoiled plasmid DNA was isolated as reported in the TAQTRAcK™ sequencing manual (Promega Ltd, Southampton, UK). 5 µg denatured plasmid was sequenced using the chain-termination method of Sanger et al, *Proc. Natl. Acad. Sci.* 74 5463–5467 (1977) using the sequencing kit SEQUENASE™ v.2.0, (USB, c/o Cambridge BioScience, UK). Compressions were resolved by performing the reactions at 70° C. using Taq DNA polymerase (TAQTRACK™ sequencing kit, Promega). DNA sequences were analysed using the University of Wisconsin Genetics Computer Group (UWGCG) package (Devereux et al, *Nucl. Acids Res.* 12 387–395 (1984)) and the DNA Strider program (Marck, *Nucl. Acids Res.* 16 1829–1836 (1988)).

Isolation of cDNA clones by differential screening cDNA clones of mRNAs accumulating preferentially in the dehiscence zones of developing pods were identified using a differential screening strategy. This employed random-primed, radio-labelled cDNAs generated from poly (A)+ RNA, isolated from the bulked 40, 45 and 50 DAA samples of the pod containing the dehiscence zone and from adjacent tissue lacking this zone (see FIG. 1). Any potential positives were confirmed by isolation and rescreening at lower densities. By this method 36 clones were isolated from screening 150,000 recombinants, which on cross-hybridization could be grouped into 13 families. When screened with the insert from the clone designated pSAC51, 19 other clones were shown to have homology (data not shown), indicating that this cDNA may encode an abundant mRNA. The insert from pSAC51 was approximately 700 bp in length by comparison with DNA standards on an ethidium bromide stained agarose gel.

pSA C51 mRNA expression by Northern analysis

Figure 1:
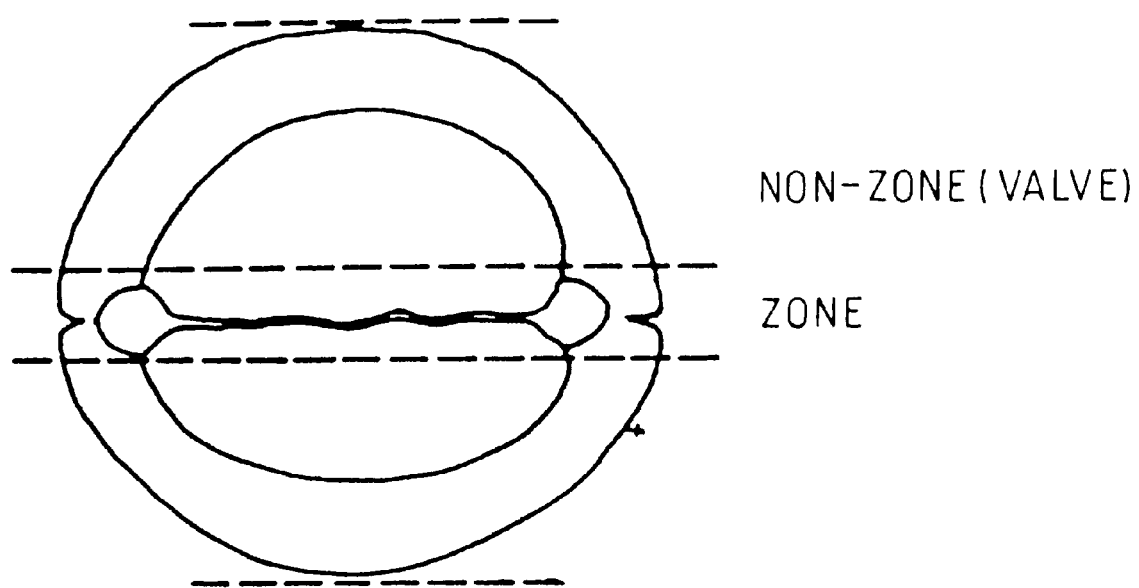
FIG. 1 relates to Example 1 and is a diagrammatic representation of a transverse section through an oilseed rape pod showing the distinction between 'zone' and 'non-zone' pericarp tissue used for protein extraction.

Pods were harvested at 20, 40, 45, 50, 60 DAA and dehiscence zone (Z) and flanking non-zone (NZ) tissue isolated (see FIG. 1). Total RNA was extracted from these excised parts and from the seed, leaves and roots. Northern analysis revealed that the 700 bp insert from pSAC51 hybridised to a mRNA of about 700 nucleotides (See FIGS. 2A and 2B). At 20 DAA hybridisation was apparent in both Z and NZ, but subsequently disappeared in NZ tissues and preferentially accumulated in the dehiscence zone tissue with maximum signal occurring at 60 DAA. The process of dehiscence is visible to the naked eye at 50 DAA. The transcript could not be detected in the leaves, seeds and roots. The cDNA pSAC51 was deemed to be near full-length because the mRNA transcript size was similar to that of the cDNA insert size.

pSAC51 sequence and amino acid analysis

Both strands of the cDNA were sequenced and the result is shown in FIG. 3 (SEQ ID NO:1). When sequenced the cDNA was 756 bp in length. The largest open reading frame (ORF) was 441 nucleotides in length beginning at position 15 (A) and ending at position 456 (T). The deduced protein sequence of 147 amino acids (SEQ ID NO:1,2) has a calculated molecular mass of approximately 15 kDa and rich in proline (14.2%), leucine (14.2%) and lysine (10.2%). At the end of the nucleotide sequence there was a large poly(A) tail that encompassed 42 (A) nucleotides. A prominent feature of the pSAC51 deduced amino acid sequence was the arrangement of the proline residues into the repeated motif "Pro-X" (underlined in FIG. 3). The sequence also contains a potential glycosylation site denoted by the motif "N-X-S or T" (Kornfeld and Kornfeld, Ann. Rev. Biochem. 54 631–664 (1985)) and a possible polyadenylation site (Joshi, Nucl. Acids Res. 15 9627–9640 (1987)).

The hydropathy plot (FIG. 4) of the peptide indicates that the protein has several distinct domains. The protein has a hydrophobic amino terminus, characteristic of a membrane spanning cleavable signal sequence (von Heijne, Nucl. Acids Res. 144683–4690 (1986)), extending to position 30. It then has a hydrophilic region extending to position 70, followed by a further hydrophobic region extending to the carboxy terminus.

Analysis of this sequence utilising the UWGCG programs revealed the protein to share significant homology with several proteins; 57% with a carrot cDNA (DC2.15) representing a mRNA that accumulates during somatic embryogenesis (Aleith and Richter, Planta 183 17–24 (1990)); 40% with a cDNA (pZRP3) that represents a mRNA localised to cortical cells in maize roots (John et al, Plant Mol. Biol. 20 821–831 (1992)). A comparison of the sequences of these proteins (SEQ ID NO:4,5) with that deduced from the nucleotide sequence of pSAC51 (SEQ ID NO:3) is shown in FIG. 5. The deduced amino acids share similar compositions and hydropathy plots. They also have the "Pro-X" domain within the first 50 amino acids and a characteristic DALK motif underlined in FIG. 5.

Genomic Southern analysis of pSAC51

The 756 bp insert of pSAC51 was used as a probe for hybridisation to Southern blots of B. napus genomic DNA digested with EcoRI, HindIII and BamHI (FIG. 6). The probe hybridised to several fragments ranging in size from 5 kb to 1 kb. The cDNA has an internal restriction site for HindIII at nucleotide 32 and this may account for extra fragments.

Discussion

Pod dehiscence is a hard phenotype to measure accurately and therefore the precise start of the process is not known. Cellulase activity increases in the dehiscence zone from 40 DAA and precedes the first visible signs of cell wall breakdown by 15–20 days (Meakin and Roberts, J. Exp. Bot. 41 1003–1011 (1990)). Therefore mRNA extracted from different developmental stages (40, 45 and 50 DAA) were bulked in order to increase the chances of obtaining mRNAs that are present prior to and during the process of dehiscence. As the pods develop on an oilseed rape plant they undergo growth and expansion (Meakin, The physiology of bud abscission and pod shatter in oilseed rape (Brassica napus L.) PhD Thesis, University of Nottingham, UK (1988)) which then stops at 20 DAA. After this point the pods do not increase in size as the priority becomes seed expansion and filling. During this time the pods are drying out and losing chlorophyll (Meakin, The physiology of bud abscission and pod shatter in oilseed rape (Brassica napus L.) PhD Thesis, University of Nottingham, UK (1988)). Concurrent with this is the process of pod dehiscence (Meakin and Roberts, J. Exp. Bot. 41 995–1002 (1990)).

This example relates to the isolation of a cDNA clone that corresponds to a mRNA that preferentially accumulates in the dehiscence zone of the developing pod (FIGS. 2A and 2B). The pSAC51 mRNA is present at the early stages of pod development in both the zone and non-zone tissue. The presence of signal in the non-zone RNA at 20 DAA cannot be fully explained. Genomic Southern analysis (FIG. 6) shows that pSAC51 may be controlled by a single or a small family of genes and the presence and/or arrangement of introns has yet to be determined. Therefore the presence of some hybridising bands may be due to further restriction sites in the genomic sequence. Also B. napus (n=19) is an amphidiploid resulting from a natural interspecific hybridisation even between B. oleracea (n=9) and B. campestris (n=10) and the resulting genome is likely to contain 2 copies of any gene, one from each parental genome.

The deduced protein sequence (SEQ ID NO:1,2) of pSAC51 has several features that are worth mentioning (FIG. 3). The protein is rich in the amino acid, proline, whose arrangement is in the form of a repeated motif "Pro-X". It also has another arrangement of amino acids into a "DALK" motif. Other characteristics include defined hydrophobic and hydrophilic domains (FIG. 4) and a membrane spanning cleavable signal peptide. The pSAC51 deduced amino acid sequence (SEQ ID NO:3) has an unknown function but has significant homology to other characterised proteins (SEQ ID NOs:4,5) whose functions are also unknown (FIG. 5). These proteins are from different plant species and from different plant organs; carrot embryos (Aleith and Richter, Planta 183 17–24 (1990)) and young maize roots (John et al, Plant Mol. Biol. 20 821–831 (1992)). The pSAC51 protein also has significant homology (>40%) with a protein of unknown function from immature tomato fruit (Salts et al, *Plant Mol. Biol.* 17 149–150 (1991)). This protein is also rich in proline (but has a different arrangement) and has a pronounced hydrophobic domain as well as the "DALK" motif but the cDNA and protein is much larger. Sequence alignment analysis shows the homology to be with proline residues and with the hydrophobic domain particularly with the cysteine residues. There are also other proteins that have significant homology with pSAC51 and were isolated from soybean seeds (Odani et al, *Eur. J. Biochem.* 162 485–491 (1987), Estanyol et al, *Plant Cell* 4 413–423 (1992)). Again they are proline-rich and have hydrophobic domains. This may give some insight into the role of the protein encoded by pSAC51 in that it may be connected with the developing seed. Given that the pSAC51 protein is likely to be transported and that the seed attachments to the pod occur in the region of the dehiscence zone then it may have a role in seed development, although no pSAC51 mRNA was detected by Northern analysis.

The processes of abscission and dehiscence involve the breakdown of cell walls. The cell walls of a plant are composed of cellulose, hemicellulose, pectic compounds, proteins, suberin, lignin and water (Cassab and Verner, *Ann. Rev. Plant Physiol. Plant Mol. Biol.* 39 321–353 (1988)), but can be grouped into three main types: hydroxyproline-rich glycoproteins (HRGPs) (Chen and Varner, *Proc. Natl. Acad. Sci.* 82 4399–4403 (1985), Zheng-Hua and Varner, *Plant Cell.* 3 23–37 (1991)); glycine-rich proteins (GRPs) (Condit and Meagher, *Nature* 323 178–181 (1986)); and lastly proline- (or hydroxyproline)-rich proteins (PRPs) (Hong et al, *Plant Cell* 1 937–943 (1989), Wyatt et al, Plant Cell 4 99–110 (1992)). All these proteins are characterised by basic repeat motifs that are different for each type: Ser-(Hyp)$_4$ for HRGPs; (Gly-X)$_n$ for GRPs; and Pro-Pro-Val-X-Y for PRPs. The proline-rich protein encoded by pSAC51 shows no significant identity to any of the aforementioned groups described so far (Cassab and Varner, *Ann. Rev. Plant Physiol. Plant Mol. Biol.* 39 321–353 (1988)). The proline-rich proteins that do show homology to pSAC51 have all been characterised since that review was written and, given the different proline repeat motif "Pro-X", they may be a new sub-group of proline-rich proteins. Despite these differences pSAC51, and the other proteins it shares homology with, do have elements that link them to the other groups of proline-rich proteins. They often include signal sequences, glycosylation sites and are expressed in specific organs and tissues. The pSAC51 deduced amino acid sequence has one glycosylation site as does the maize protein (John et al, *Plant Mol. Biol.* 20 821–831 (1992)) but the tomato (Salts et al, *Plant Mol. Biol.* 17 149–150 (1991)) and carrot (Aleith and Richter, *Planta* 183 17–24 (1990)) proteins do not. Many proline-rich proteins that have been characterised so far have been isolated from tissue capable of growth and cell expansion and they may have a role in cell wall formation and structure (Cassab and Varner, *Ann. Rev. Plant Physiol. Plant Mol. Biol.* 39 321–353 (1988)). Others have been found to be produced in response to wounding and stress signals (Zhous et al, *Plant Mol. Biol.* 20 5–17 (1992)). The pSAC51 mRNA is present and increases when the pod has stopped growing and so the protein translated from this may be involved in some other process, for example, pod dehiscence. More and more proline rich proteins are being isolated and characterised (Cheung et al, *The Plant J.* 3 151–160 (1993), Estanyol et al, *Plant Cell* 4 413–423 (1992), Roberts et al, *The Plant J.* 3 111–120 (1993), Wright et al, *The Plant J.* 3 41–49 (1993)) and this may help in assigning precise functions for these unknown proline-rich proteins.

EXAMPLE 2

Cloning of pSAC25/pSAC40

Following the general procedure of Example 1, other cDNAs were cloned. One was designated pSAC25, which has a different pattern of gene expression from that of pSAC51. pSAC40 is one of several cDNAs with sequences that match pSAC25: the insert is slightly larger than pSAC25.

Pods were harvested at 20, 30, 35, 40, 45, 50 and 60 DAA, and dehiscence zone and flanking non-zone tissue isolated, as described in Example 1. Northern analysis of extracted RNA reveals that expression was taking place in zone tissue from 30 DAA, with only slight expression in non-zone tissue as late as 50 DAA (FIGS. 7A and 7B). The transcript could not be detected in leaves, seeds or roots.

The cDNA sequence of pSAC40 was sequenced and the result, with the deduced amino acid sequence (SEQ ID NO:6), is shown in FIGS. 8A and 8B. The hydropathy plot (FIG. 9) of the deduced amino acid sequence (SEQ ID NO:6,7) shows distinct hydrophobic and hydrophilic regions.

Genomic Southern analysis of pSAC25

The insert of pSAC25 was used as a probe for hybridisation to Southern blots of *B. napus* genomic DNA digested with EcoRI, HindIII and BamHI. The probe hybridised to several fragments ranging in size from 7 or 8 kb to 1 kb.

EXAMPLE 3

Cloning of gSAC51 and gSAC51 a) Isolation and characterisation of the SAC25 gene.

A 10 kb A. thaliana genomic clone [gSAC25] was isolated that hybridised to the pSAC25 cDNA (FIG. 11A). A 3.5 kb EcoRI/HindIII fragment of this DNA that hybridised to the pSAC25 cDNA was subcloned into EcoRI/HindIII cut pBluescript KS+, forming pDH30. Nucleotide sequencing shows that this fragment contains an ORF that is highly homologous to the pSAC25 ORF. This sequence also determines the position of the SAC25 promoter region relative to the SAC25 ORF, as it is that region upstream of (ie 5' to) the ORF.

b) Isolation and characterisation of the SAC51 gene.

A 10 kb A. thaliana genomic clone [gSAC51] was isolated that hybridised to the pSAC51 cDNA (FIG. 11 B). A 4.0 kb EcoRI fragment of this DNA that hybridised to the pSAC51 cDNA was subcloned into EcoRI cut pBluescript KS$^+$, forming pDH31. Nucleotide sequencing shows that this fragment contains an ORF that is highly homologous to the pSAC51 ORF. This sequence also determines the position of the SAC51 promoter region relative to the SAC51 ORF, as it is that region upstream of (ie 5' to) the ORF.

EXAMPLE 4

Use of SAC25 and SAC51 promoters

To demonstrate that the putative promoter regions of SAC25 and SAC51 are capable of driving the expression of a foreign gene in *A. thaliana, B. napus* and *N. tabacum,* transcriptional fusions of the promoters can be made to the *E. coli* gene encoding β-glucuronidase (GUS). Fragments of the clones [gSAC25] or [gSAC51] containing the putative promoter region are subcloned into pBI101 (Jefferson et al, *EMBO J.* 6 3901 (1987)). The GUS constructs are then transformed into *A. thaliana, B. napus* or *N. tabacum,* using standard transformation techniques. Analysis of the transformed plants demonstrates that GUS activity is localised to the pod shatter zone. The temporal regulation of GUS activity will be identical to the temporal expression observed for the SAC25 and SAC51 genes as described in Examples 1 and 2.

EXAMPLE 5

The Construction of Expression Cassettes and their use in Producing Sense and Anti-Sense RNA to Pod Shatter Zone-Specific Messages in Transgenic Plants Either pod shatter zone-specific or constitutive promoters can be used to drive expression of sense or anti-sense RNA corresponding to shatter zone-specific transcripts in transgenic plants, thus potentially creating pod mutations and shatter-resistance (indehiscence). The same pod shatter zone-specific promoters can be used to drive the pod shatter zone expression of genes encoding proteins or enzymes detrimental to shatter-zone function thereby creating shatter-resistance (indehiscence).

a) Construction of an Intermediate Vector to Express Sense and Anti-Sense RNA Utilising the Double 35S Promoter A 650 bp HindIII, EcoRI SAC25 fragment from the SAC25 cDNA was cloned into HindIII, EcoRI-cut pJIT60 forming p35S-antiSAC25 (FIG. 12). pJIT 60 is identical to pJIT30 (Guerineau et al, *Plant Mol. Biol.* 15 127–136 (1990)) except that the CaMV 35S promoter is replaced by a double CaMV 35S promoter. In p35S-antiSAC25 a portion of the SAC25 cDNA is cloned in an antisense orientation between a double 35S promoter and a CaMV polyadenylation signal. This chimeric gene was then cloned into pBin19 (Bevan et al, *Nucl. Acids Res.* 22 8711–8721 (1984)) as a Ssn, XhoI fragment forming p35S-antiSAC25. *B. napus* plants transformed with the 35S-antiSAC25 chimeric gene are resistant to pod-shatter (indehiscent).

Other chimeric genes that can be constructed to produce shatter-resistance include, by way of non-limiting example:

i) Double CaMV 35S promoter linked to the coding region of the SAC25 cDNA or gene such that sense SAC25 RNA is produced;

ii) Double CaMV 35S promoter linked to the coding region of the SAC51 cDNA or gene such that sense or anti-sense SAC51 RNA is produced;

iii) SAC25 promoter linked to the coding region of the SAC25 cDNA or gene, such that sense or anti-sense SAC25 RNA is produced;

iv) SAC51 promoter linked to the coding region of the SAC25 cDNA or gene, such that sense or anti-sense SAC25 RNA is produced;

v) SAC25 promoter linked to the coding region of the SAC51 cDNA or gene, such that sense or anti-sense SAC51 RNA is produced; and vi) SAC51 promoter linked to the coding region of the SAC51 cDNA or gene, such that sense or anti-sense SAC51 RNA is produced.

These plasmids could also be transformed into other members of the Brassicaceae causing shatter-resistance in the transgenic plants.

The utility of the SAC25 and SAC51 promoters could also be harnessed by expressing gene fusions to barnase, or other genes that disrupt cellular development or otherwise interfere in the function of the shatter zone in pod shatter, in transgenic plants. Use of the barnase gene to cause cell ablation has been described in EP-A-0344029 (Plant Genetic Systems NV) and WO-A-9211379 (Nickerson International Seed Company Limited), particularly at pages 28 and 29 of the latter document.

Transcriptional or translational fusion of the SAC25 or SAC51 promoter fragments and the transfer of these genes into *B. napus* or *N. tabacum* plants results in ablation of the pod shatter zone causing shatter-resistance.

We claim:

1. An isolated nucleic acid which:
   (a) comprises the sequence in FIG. 3 (SEQ ID NO:1) or FIGS. 8A and 8B (SEQ ID NO:6); or
   (b) encodes the amino acid sequence of FIG. 3 (SEQ ID NO:2) or FIG. 8 (SEQ ID NO:7).

2. The nucleic acid as claimed in claim 1 operatively coupled to a promoter in the sense or antisense orientation.

3. The nucleic acid as claimed in claim 2, wherein the promoter is the CaMV 35S, rubisco or plastocyanin promoter.

4. The nucleic acid as claimed in claim 2 or claim 3, wherein said nucleic acid is also operatively coupled to a 3'-transcriptional regulatory signal.

5. The nucleic acid as claimed in claim 1, which has the sequence of SEQ ID NO: 1, and which encodes a protein having the amino acid sequence shown in FIG. 3 (SEQ ID NO:2).

6. The nucleic acid as claimed in claim 1, which has the sequence of SEQ ID NO:6, and which encodes a protein having the amino acid sequence shown in FIGS. 8A and 8B (SEQ ID NO:7).

7. A vector comprising the nucleic acid as claimed in claim 1.

8. A host cell transfected or transformed with the nucleic acid as claimed in claim 1.

9. A plant cell transformed with the nucleic acid as claimed in claim 1.

10. A transgenic plant regenerated from the plant cell as claimed in claim 9, or a part of said plant.

* * * * *